(12) United States Patent
Segall (10) Patent No.: US 9,581,556 B1
(45) Date of Patent: Feb. 28, 2017

(54) LASER PROBE FOR USE IN AN INSPECTION SYSTEM

(71) Applicant: Industrial Optical Measurement Systems, Ann Arbor, MI (US)

(72) Inventor: Stephen Barrett Segall, Ann Arbor, MI (US)

(73) Assignee: Industrial Optical Measurement Systems, LLC, Ann Arbor, MI (US)

( * ) Notice: Subject to any disclaimer, the term of this patent is extended or adjusted under 35 U.S.C. 154(b) by 17 days.

(21) Appl. No.: 14/802,603

(22) Filed: Jul. 17, 2015

Related U.S. Application Data (63) Continuation-in-part of application No. 14/081,650, filed on Nov. 15, 2013, now Pat. No. 9,134,232.

(60) Provisional application No. 61/726,826, filed on Nov. 15, 2012.

(51) Int. Cl.
*G01N 21/55* (2014.01)
*G01N 21/21* (2006.01)
*G01N 21/954* (2006.01)

(52) U.S. Cl.
CPC ... *G01N 21/954* (2013.01); *G01N 2021/9546* (2013.01); *G01N 2021/9548* (2013.01); *G01N 2201/0683* (2013.01)

(58) Field of Classification Search
CPC ............................. G01N 21/55; G01N 21/21
USPC ......................... 356/602, 608, 634
See application file for complete search history.

(56) References Cited

U.S. PATENT DOCUMENTS

| | | | |
|---|---|---|---|
| 3,761,186 A * | 9/1973 | Wason | G02B 23/2407 356/241.1 |
| 4,055,382 A | 10/1977 | Ziekman et al. | |
| 4,315,688 A | 2/1982 | Pryor | |
| 4,440,496 A | 4/1984 | Milana | |
| 4,461,569 A | 7/1984 | Corbett | |
| 4,505,585 A | 3/1985 | Yoshikawa et al. | |
| 4,508,450 A | 4/1985 | Ohshima et al. | |
| 4,555,727 A | 11/1985 | Nun et al. | |
| H230 H * | 3/1987 | Smith | G01N 21/954 356/364 |
| 4,669,885 A | 6/1987 | Ina | |
| 4,732,474 A | 3/1988 | Chikama | |
| 5,033,856 A * | 7/1991 | Nose | G01B 11/24 250/201.2 |
| 5,054,087 A | 10/1991 | Carbon et al. | |
| 5,315,374 A | 5/1994 | Yoshizumi | |
| 5,317,387 A * | 5/1994 | Van Hengel | G01N 21/88 356/446 |
| 5,353,357 A | 10/1994 | Longest, Jr. et al. | |

(Continued)

*Primary Examiner* — Roy M Punnoose
(74) *Attorney, Agent, or Firm* — Vivacqua law, PLLC; Raymond J. Vivacqua; John M. Card (57) ABSTRACT

A non-contact optical probe for inspecting an inside surface of a cylindrical workpiece includes a laser source that emits an incident light beam, a polarizing beam splitter that transmits one polarization of the incident beam and reflects the opposite polarization, and a quarter wave plate that together with the polarizing beam splitter separates back reflected return light from the incident laser beam. The non-contact optical probe further includes an optical system that directs the incident laser beam onto the cylinder surface and directs reflected light from the surface back to the beam splitter, and at least one detector that receives a portion of the reflected light and generates data about the cylinder surface.

20 Claims, 4 Drawing Sheets

(56) References Cited

U.S. PATENT DOCUMENTS

| | | | |
|---|---|---|---|
| 5,424,834 A * | 6/1995 | Akedo | G01B 11/026 356/127 |
| 5,585,917 A | 12/1996 | Woite et al. | |
| 5,588,068 A | 12/1996 | Longest et al. | |
| 5,636,024 A | 6/1997 | Crookham et al. | |
| 5,646,724 A | 7/1997 | Hershline | |
| 5,936,725 A | 8/1999 | Pike et al. | |
| 6,097,482 A | 8/2000 | Smith et al. | |
| 6,169,600 B1 | 1/2001 | Ludlow | |
| 6,516,083 B1 | 2/2003 | Bonechi et al. | |
| 6,603,540 B1 | 8/2003 | Kaupp | |
| 6,661,508 B2 | 12/2003 | Eytan et al. | |
| 7,027,145 B2 | 4/2006 | Segall et al. | |
| 7,327,447 B2 | 2/2008 | Ovadia | |
| 7,342,654 B2 | 3/2008 | Laue et al. | |
| 7,372,557 B2 | 5/2008 | Oomori et al. | |
| 7,394,530 B2 | 7/2008 | Budd | |
| 8,928,891 B2 * | 1/2015 | Van Amstel | G01B 11/2441 356/510 |
| 2001/0015804 A1 | 8/2001 | Doyle, Jr. | |
| 2004/0201856 A1 * | 10/2004 | Quadling | G01B 11/2518 356/601 |
| 2011/0080588 A1 | 4/2011 | Segall | |

\* cited by examiner

LASER PROBE FOR USE IN AN INSPECTION SYSTEM

CROSS-REFERENCE TO RELATED APPLICATIONS

This application is a continuation-in-part application of U.S. patent application Ser. No. 14/081,650, filed on Nov. 15, 2015, which claims the benefit of U.S. Provisional Patent Application No. 61/726,826, filed on Nov. 15, 2012. The entire contents of the above applications are incorporated herein by reference.

FEDERALLY SPONSORED RESEARCH

Certain of the research leading to the present invention was sponsored by the United States Government under National Science Foundation Grant IIP-0739472. The United States Government has certain rights to the invention.

FIELD

The present disclosure relates to non-contact laser inspection systems and more particularly to non-contact laser inspection systems for detection of surface defects on reflective or partially reflective cylindrical or cylindrically symmetric parts.

BACKGROUND

High volume automated manufacturing systems are very good at producing large numbers of identical interchangeable parts. However, unless there is adequate inspection of the output of these systems, if they drift out of compliance and start producing parts that are out of tolerance or start producing defective components due to chipped tools or other causes, they can produce very large quantities of identical defective parts before the problem is detected. The material from which a part is produced can also contain defects, such as pores or scratches that would cause a finished part to be rejected as defective.

If defective components enter the assembly stream for a manufactured product, such as a vehicle or appliance, the cost of detecting and correcting a defect can increase exponentially. This cost includes the cost of detecting the problem, disassembling the product to identify the component causing the problem, and identifying and correcting the source of the component defect. It may involve shutting down a production line until the source of the problem is identified and corrected. If finished products are shipped with defective components, the cost of fixing the problem could also involve product returns and warranty repairs.

There is, therefore, a high priority placed on identifying defective components at the earliest possible stage of production to minimize scrap and prevent defective components from entering the assembly stream. In a high volume automated production system inspection of parts by human inspectors is subjective and inadequate. It is preferable to have inspection techniques that can be automated to detect defects at the rate of production according to objective criteria. Non-contact inspection methods are preferred because they do not involve the use of mechanical gauges that can wear and need to be periodically replaced. Optical inspection of components is one of these non-contact inspection techniques. It is often preferred for detecting surface defects in manufactured components because it can rapidly collect and analyze high resolution data.

A number of non-contact optical devices have been developed over the past several years for the inspection of manufactured surfaces in a production environment. These can be divided into two broad categories according to the light source that is used—laser scanning devices and machine vision systems employing broadband unpolarized or white light sources. Each of these two approaches to optical inspection can be divided into two main classes of devices—those that inspect the exterior surfaces of components and those that inspect the interior surfaces. Devices that inspect exterior surfaces that are flat or have a curved profile may not be capable of inspecting the interior surfaces of cylindrical objects. Some vision systems developed for external inspection can see inside containers, but their inspection capabilities are limited, especially if a container is long and narrow, such as the case of some cylinders. However, inspection systems that can inspect the inside of cylinders may be adapted to measure the outside of cylindrical or cylindrically symmetric objects, disks or spheres.

Accordingly, there is a need in the art for an improved non-contact laser inspection system capable of rapidly detecting surface defects and surface profile variations using laser light to inspect cylinder bores.

SUMMARY

One embodiment of a non-contact optical probe for inspecting an inside surface of a cylindrical workpiece includes a laser source that emits an incident light beam, a polarizing beam splitter that transmits one polarization of the incident beam and reflects the opposite polarization, and a quarter wave plate that together with the polarizing beam splitter separates back reflected return light from the transmitted incident laser beam. The non-contact optical probe further includes an optical system that directs the transmitted incident laser beam onto the cylinder surface and directs reflected light from the surface back to the beam splitter and at least one detector that receives a portion of the reflected light and generates data about the cylinder surface.

In yet another embodiment, a non-contact probe for inspecting a cylindrical surface of a workpiece includes a laser source that emits an incident light beam, a polarizing beam splitter that transmits one direction of polarization of the incident laser beam and reflects the other direction of polarization, a quarter wave plate that converts the transmitted incident beam from linear polarization to circular polarization, a first reflector that directs the incident light beam onto a cylindrical surface and receives reflected light from the cylindrical surface, a second reflector that receives scattered light from the cylindrical surface, a first detector that receives the return reflected light from the polarizing beam splitter, and a second detector that receives scattered light from the cylinder surface that is deflected by the second reflector. The first detector and the second detector generate signals related to reflected and scattered scanning data from the surface.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

The following description is merely exemplary in nature and is not intended to limit the present disclosure, application, or uses. It is to be understood that standard components or features that are within the purview of an artisan of ordinary skill and do not contribute to the understanding of the various embodiments of the invention may be omitted from the drawings to enhance clarity. In addition it will be appreciated that the characterization of various components and orientations described herein as being "vertical" or "horizontal", "right" or "left", "side", "top" or "bottom" are relative characterizations only based upon the particular position or orientation of a given component for a particular application.

Figure 1:
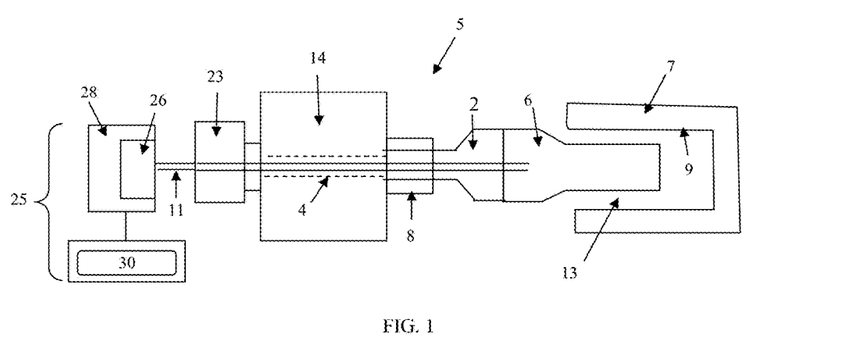
FIG. 1 is schematic drawing of an inspection system detecting back reflected light in accordance with the principles of the present invention.

With reference to FIG. 1, a schematic diagram of probe system 5 for inspecting workpiece 7 is shown. Inspection probe system 5 includes a probe body 6 mounted on probe shaft 2, which is fastened to spindle 14 by chuck, collet, tool holder or custom mounting system 8. Spindle 14 has a hollow rotor 4 that could permit electrical cables 11 for power and data transmission to pass from probe body 6 through slip ring 23 to control and processing unit 25, which includes a data acquisition unit 26, a computer 28 and a display monitor 30. Data acquisition unit 26 may be an internal data acquisition card installed in computer 28 or an external data collection unit in communication with computer 28. In other embodiments of this invention hollow rotor 4 could also be used to transmit optical signals rather than electrical signals without using a slip ring. At least one linear motion stage can be employed to move probe 5 relative to workpiece 7 for the operation of a complete inspection station.

Workpiece 7 includes an at least partially reflective inner surface 9 that defines at least one bore 13. In the example provided, bore 13 is a combustion cylinder and workpiece 7 is an engine block of an internal combustion engine. However, it should be appreciated that cylindrical bore 13 could exist in many other types of workpieces 7, such as, but not limited to, brake cylinders, shock absorbers, hydraulic or pneumatic cylinders, gas flow valves, tapped internally threaded cylinders or other cylindrical manufactured parts. The description of the invention is merely exemplary in nature and variations that do not depart from the gist of the invention are intended to be within the scope of the invention. Such variations are not to be regarded as a departure from the spirit and scope of the invention.

Figure 2:
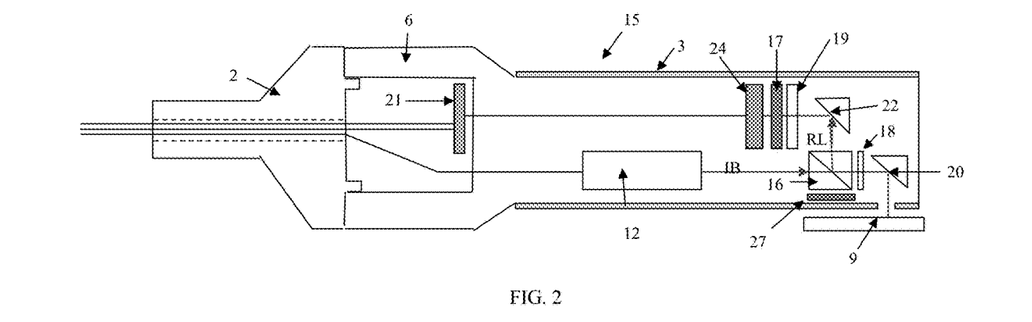
FIG. 2 is a more detailed schematic drawing of the probe of the inspection system shown in FIG. 1.

FIG. 2 shows the internal components located in probe body 6 of probe 15. Laser module 12 emits incident laser beam IB, which enters polarizing beam splitter 16. Laser module 12 may also contain focusing optics to focus incident beam IB to a small spot on cylinder surface 9. One commercial source for such a laser module is Laser Components of Hudson, NH. If laser module 12 does not contain focusing optics, optional beam reducing or focusing optics can be included following laser module 12 in probe body 6 to reduce the size of the spot illuminating cylinder surface 9. Polarizing beam splitter 16 transmits one component of polarization of incident laser beam IB and reflects light with the orthogonal polarization. Optional high-absorption neutral density filter 27 may be used as a beam dump to absorb unwanted light reflected from laser beam IB by polarizing beam splitter 16. When laser module 12 generates a linearly polarized beam of light, laser module 12 can be oriented so that the polarization of beam IB enables incident beam IB to substantially pass through polarizing beam splitter 16 without significant reflection by beam splitter 16. Quarter wave plate 18 converts incident laser beam IB that is transmitted through polarizing beam splitter 16 from linear to circular polarization. Incident beam IB that passes though quarter wave plate 18 is reflected by reflecting surface 20 and directed towards cylinder surface 9.

A portion of incident beam IB is reflected directly back from cylinder surface 9 into the optical system of probe 15 as return light RL. Return light RL is reflected by reflecting surface 20 through quarter wave plate 18 and into polarizing beam splitter 16. Quarter wave plate 18 converts the reflected return light RL from cylinder surface 9 from circular to linear polarization, but with a direction of polarization perpendicular to the incident direction of polarization, which causes the portion of return light RL with linear polarization perpendicular to the incident direction of polarization to be reflected toward mirror surface 22. Mirror surface 22 reflects return light RL towards detector 24. Before reaching detector 24 return light RL passes through wavelength filter 19 which rejects light at wavelengths other than the laser wavelength and optional neutral density filter 17, which reduces the intensity of return light RL to prevent saturation of detector 24. Laser module 12, detector 24 and the optical components of probe 15 are contained within envelope 3 that covers a portion of probe body 6 and protects the components inside from contamination, damage and electrical noise. A hole in envelope 3 permits incident beam IB to exit probe 15 and return light RL to enter probe 15 where some of return light RL is detected by detector 24. Since laser module 12, probe detector 24 and probe electronics 21 are incorporated into spinning body 6 of probe 15, slip ring 23 is employed to transmit power to probe 15 and data from probe 15. The internal structure of probe body 6 that rigidly supports each of the elements contained in probe body 6 is not shown. Also not shown are modifications to the probe body design required to keep the center of mass of the probe located on the probe axis.

A non-polarizing beam splitter could be employed without a quarter wave plate in probe 15, but much of the incident beam IB and reflected light RL would be lost and much less light would reach detector 24.

Data acquisition unit 26 may have an internal power supply and be able to provide power to laser module 12. Alternatively, a separate regulated power supply or battery could provide power to laser module 12. Other types of devices that perform the same functions as computer 28 may be employed without departing from the scope of the present invention. Data acquisition unit 26 can be in communication with a rotary encoder and a linear encoder. Data acquisition unit 26 receives signals from signal processing electronics 21 that amplifies and processes the signals from detector 24.

Data collected by scanning surface 9 of cylinder 13 using probe system 5 can be used to generate an image of surface 9 using graphics software contained in computer 28. A linear motion stage is used to move spindle 14 relative to part 7 to scan surface 9 of cylinder 13 as probe 15 rotates. Detector 24 in probe 15 collects directly back reflected and backscattered return light RL. The signal from detector 24 is sent to data acquisition system 26 after processing by electronic circuit 21 to generate an array of data values of collected light intensity from which an image of surface 9 can be produced by computer 28 and displayed on monitor 30. This image can be used to identify defects and other features on surface 9. However, probe system 5 does not measure displacement of surface 9 relative to the axis of probe 15.

For probe system 5 to work properly to generate images from scans of surface 9 of cylinder 13, the axis of probe 15 is coincident with the axis of cylinder 13 to a sufficient degree of accuracy along the length of cylinder 13. For system 5 to operate properly under factory conditions it is sufficiently insensitive to relative alignment of the probe axis and cylinder axis to produce a useful surface image for a range of normal part tolerances.

Defect detection using surface images requires contrast between defective and non-defective surface regions. For a scanning laser probe detecting back reflected light, a low reflected signal from a surface defect that scatters the incident laser light is not difficult to obtain. The light from the defect will be primarily scattered in directions that do not reach the detector. To observe the defect, a higher background signal from the non-defective area of the surface adjacent to the defect is employed. If the laser beam is not aligned properly relative to the surface, light from the non-defective surface may be reflected in directions that also do not reach the detector. If this happens it may not be possible to distinguish the signal on the detector produced by a defect from the background signal.

Sensitivity to alignment is, therefore, a key factor in the design of a probe that inspects cylinder surfaces using back reflected light. There are a number of parameters that affect sensitivity to alignment. These are:
1. The radius of curvature of the cylinder being inspected
2. The optical path length from the spot on the cylinder to the detector in the probe
3. The diameter of the sensitive area of the optical detector detecting return light
4. The rigidity of the relative alignment of the optical components in the probe as the laser beam is rotated
5. The diameter of the passageway through which the laser light must travel to the cylinder and back to the detector A cross section of a cylinder perpendicular to the axis of the cylinder is a circle, so in this cross section a reflective or partially reflective cylinder surface is like a mirror with a constant radius of curvature. A laser beam in this plane that is incident perpendicular to the axis of the cylinder will focus at a distance one diameter from the surface and diverge from that point.

The larger the radius of curvature of the cylinder, the less sensitive the probe is to alignment errors of the part relative to the probe in the plane perpendicular to the axis of the cylinder. Light reflected from the surface focuses and diverges over a greater distance in the plane perpendicular to the cylinder axis when the radius of curvature is larger, so the chances of non-optimally-incident light reflected from non-defective surfaces reaching the detector is better, improving the contrast between defects and the non-defective background surface.

An inspection system for inspecting the inside surface of cylinders must be designed to inspect the cylinder diameter it is expected to measure. Cylinder diameter is, therefore, a given and cannot be varied by the inspection system. The alignment parameters that can be controlled in the inspection system design are the optical path length from the cylinder surface to the detector and the size of the detector. Given a cylinder diameter, the distance from cylinder surface 9 to detector 24 can be minimized and the size of detector 24 can be maximized (consistent with other constraints) to minimize sensitivity to alignment. The distance from the spot on cylinder surface 9 to detector 24 together with the diameter of the sensitive area of detector 24 define the solid angle within which the return light signal RL can be detected by detector 24.

Also, the smaller the focused spot on cylinder surface 9 the better the resolution. However, even when the spot on cylinder surface 9 is large, much of the light that is not normally incident to the surface may miss the sensitive area of detector 24, which will make the effective spot size at the location of normal incidence smaller and improve the resolution.

In a plane containing the axis of a cylinder, the surface of the cylinder intersected by this plane is a straight line that acts like a flat mirror with the angle of incidence equal to the angle of reflection.

The closest distance detector 24 can be located relative to a spot on cylindrical surface 9 is at the end of probe 15. Here the distance from surface 9 of cylinder 13 to detector 24 is minimized and the sensitivity to alignment is minimized. This is the reason detector 24 in FIG. 2 is located at the end of probe 15 closest to the illuminating spot on cylinder surface 9. However, the diameter of cylinder 13 must be large enough to insert probe 15 into cylinder 13. If the diameter of the cylinder being inspected is sufficiently large, the diameter of the probe body might even be increased to allow a detector with a larger sensitive area to be incorporated into the probe body to collect background light that might miss the sensitive area of a smaller diameter detector.

Another advantage of the design of FIG. 2 is that the optical components are rigidly aligned relative to each other inside probe 15. This means that if the probe is properly aligned along one diameter of a plane perpendicular to the axis of a cylinder, rotating the probe will not affect the alignment. Because the distance between surface 9 and detector 24 is relatively short, focused incident laser beam IB can practically be at its minimum diameter, so that only a small diameter passage is needed to ensure that beam IB does not clip the sides of the holes through which it is transmitted.

Figure 3:
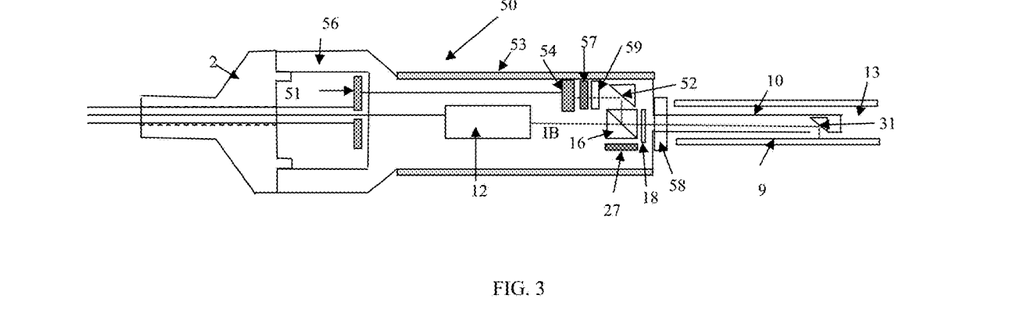
FIG. 3 is a schematic drawing of yet another inspection probe design detecting back reflected light in accordance with the principles of the present invention.

While probe 15 employs optimized design principles to minimize sensitivity to alignment, the inside diameter of a cylinder may be too small to inspect using probe 15. In that case, a modified probe 50, in which a small diameter extension tube 10 is mounted on the end of probe body 56, can be used to inspect the inside diameter of cylinder 13. A schematic diagram of probe 50 is shown in FIG. 3. Examples of cylinders that may need this type of probe include but are not limited to automatic transmission valve ports, fuel injectors and valve guides of internal combustion engines.

In FIG. 3, probe shaft 2, laser module 12, optional high-absorption neutral density filter 27, beam splitter 16, quarter wave plate 18, incident beam IB and cylinder surface 9 refer to the same features as in FIG. 2. Reflector 52, wavelength filter 59, optional neutral density filter 57, detector 54 and electronic circuit 51 have the same functions as reflector 22, wavelength filter 19, neutral density filter 17, detector 24 and electronic circuit 21 in FIG. 2, but may be sized and located differently to better fit into probe body 56.

In FIG. 3, probe body 56 of probe 50 has an extended hollow tip 10 that is attached to the end of probe body 56 with collet or other custom fixture 58. While tip 10 need not be centered along the axis of probe 50, since it is less robust than the rest of probe body 56, the most stable location for rotating probe tip 10 is along the axis of probe 50. Laser module 12 is also preferentially located along the axis of probe 50. Laser module 12 emits laser beam IB that travels through polarizing beam splitter 16 and quarter wave plate 18. Beam IB then travels down tip 10 to reflective surface 31, which may be the surface of a rod mirror. For intersecting cylinder surface 9 at normal incidence, the mirror would be at a 45° angle. Return Light RL back reflected and back scattered from cylinder surface 9 would be reflected by mirror surface 31 through quarter wave plate 18.

In probe 50 envelope 53 does not have a hole for light to pass through because probe tip 10 has a hole opposite reflective surface 31 to perform this function. Probe 50 can also be used to inspect large diameter cylinders, but care must be taken to ensure that the centroid of return light RL is centered over the entrance hole of tip 10.

At least part of return light RL is converted from circular to linear polarization at a polarization angle perpendicular to the polarization angle of incident beam IB. At least part of return beam RL is, therefore, reflected by polarizing prism 16 to reflective surface 52, which directs reflected light RL through wavelength filter 59 and optional neutral density filter 57 to detector 54.

Probe 50 of FIG. 3 extends the optical path length between surface 9 and detector 54 compared with the optical path length from surface 9 to detector 24 in probe 15, but probe 50 maintains the rigid alignment between the optical components as in probe 15, which helps to maintain alignment with respect to cylinder surface 9 as probe 50 spins. Probe 50, like probe 15, employs some means of providing power and transmitting data from a rapidly rotating probe containing a laser module, electronic and optical components mounted on a spindle to a data acquisition system and computer. This can again be accomplished using slip ring 23.

Beam IB entering probe tip 10 is sufficiently narrow that it is not clipped by the entrance hole of tip 10. This can be accomplished using a narrow parallel laser beam for incident beam IB or by using a focused laser beam that is already sufficiently narrow when it enters tip 10. A focused beam provides the highest resolution. If a narrower tip is required at the end of a cylinder than at the entrance, tip 10 can be made of telescoping segments so that IB passes through the entrance of tip 10 without clipping, but can also be focused to a small diameter by mirror 31.

To prevent grazing incidence light scattered from the wall of tip 10 that may be included in return light RL from entering detector 54, the inside surface of tip 10 can be tapped to produce a fine thread that scatters grazing incidence light into larger angles that miss the detector. The inside surface of tip 10 can also be blackened, for example, by being black oxidized, to absorb scattered light. Return light RL reflected from beam splitter 16 can be directed into detector 54 by an additional reflector 52. However, if there is sufficient space available in probe body 56, detector 54 can be oriented to directly observe the light reflected by beam splitter 16 after it passes through wavelength filter 59 and optional neutral density filter 57.

When laser module 12 and polarizing prism 16 are located at or near the center of the probe, space can be made available to include a second detector. This is shown in probe design 505 of FIG. 4. Detector 507 detects reflected light returning from cylinder surface 9. However, surface 9 also scatters incident beam IB in a number of different directions. A second detector 509 can be included in probe 505 to collect some of the light SL scattered by cylinder surface 9. Both detectors 507 and 509 can be photodiodes or photodiodes with integrated preamplifiers. One source for photodiodes with integrated preamplifiers is the UDT division of OSI that manufactures a line of Photops photodiode-amplifier hybrids.

A configuration that detects scattered light is described in U.S. Pat. No. 7,027,145, the entire contents of which are incorporated herein by reference. The innovation relative to U.S. Pat. No. 7,027,145 in the current invention is that the signal from a single incident beam IB can be used to simultaneously obtain measurements from both reflected and scattered light.

Figure 4:
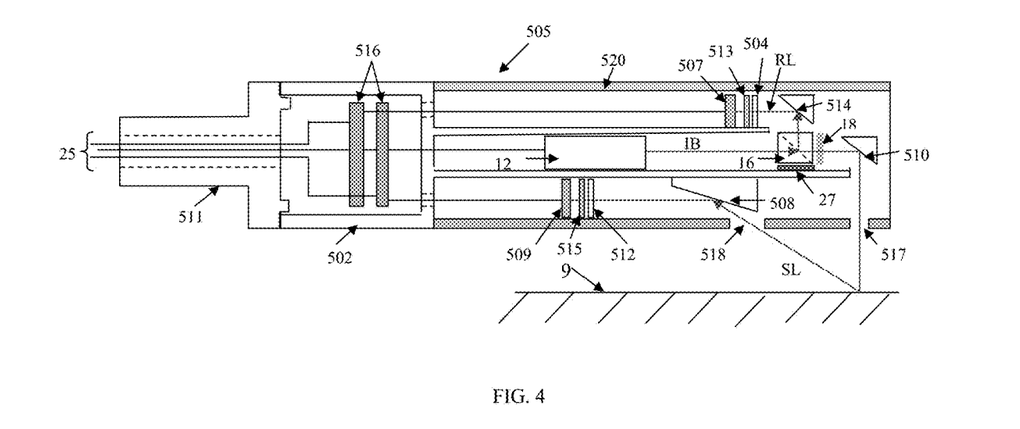
FIG. 4 is a schematic drawing of a hybrid probe design incorporating a single incident laser beam, a system for detecting back reflected light and a second system for simultaneously detecting scattered light in accordance with the principles of the present invention.

For the scattered light measurement, mirror surface 508 deflects scattered light SL from cylinder surface 9 onto detector 509 after scattered light SL passes through wavelength filter 512 and optional neutral density filter 515. Mirror 508 can be moved closer to or farther from detector 509 to collect scattered light at the same mean angle for different diameter cylinders 13.

Probe envelope 520 is used to cover and protect the section of the probe containing laser module 12, optical components and detectors 507 and 509. Envelope 520 has hole 517 to permit incident beam IB to reach cylinder surface 9 and permit reflected return light RL to enter probe body 502, be reflected by mirror surface 510, travel back through quarter wave plate 18 and polarizing beam splitter 16 and be reflected by mirror surface 514 onto detector 507 after passing through wavelength filter 504 and optional neutral density filter 513. Envelope 520 also has slit 518 to permit scattered light SL from cylinder surface 9 to reach mirror surface 508 and be directed onto detector 509 after passing thought wavelength filter 512 and optional neutral density filter 515.

A pentaprism can be used instead of reflecting surface 510 to reflect incident beam IB and return light RL. An advantage of using a pentaprism to reflect incident beam IB is that even if the pentaprism is slightly misaligned, light from laser module 12 is reflected at a 90° angle relative to the direction of incident beam IB. If a pentaprism is used instead of mirror surface 510, the transmitting faces of the pentaprism is desirably anti-reflection coated to minimize the fraction of incident beam IB reflected from the air-glass interfaces of the pentaprism back to reflected light detector 507, since detector 507 detects the sum of the signals from cylinder surface 9 and the air-glass interfaces of the pentaprism. The pentaprism also increases the optical path length between cylinder surface 9 and detector 507, which increases sensitivity to alignment for the reflective measurement.

The signals from detectors 507 and 509 are processed by electronic circuits 516 mounted in probe body 502. The electronic signals, proportional to detected laser intensity, are transmitted though probe mounting shaft 511, through rotor 4 of spindle 14 on which shaft 511 is mounted, and through slip ring 23 to data collection, analysis and display system 25.

A probe that can perform two types of measurements simultaneously can be used to measure different properties of the same cylinder surface. For example, while a probe that detects back reflected light can detect machining marks, a probe that detects scattered light may provide better resolution of some machining mark patterns and help to more easily identify defective honing patterns. However, combustion cylinders are often also plateau honed after conventional honing which does not change the honing pattern, but smoothes microscopic sharp peaks generated by the previous honing process. Plateau honing can reduce friction between piston rings and the cylinder wall when an internal combustion engine is operating, while still permitting honing grooves to retain lubricant as the piston moves up and down inside the cylinder. The more a cylinder is plateau honed, the greater the coefficient of reflectivity of the surface. The amount of plateau honing is a parameter that manufacturers wish to optimize. A probe that measures reflectivity can be used to measure the coefficient of reflectivity of these plateau honed cylinders and relate this to the amount of plateau honing in the cylinder.

All of the probe embodiments described up to this point for inspecting the inside of cylinders employ probes in which the laser module, detectors and electronic circuits spin with the probe. These probes usually employ a slip ring to transmit power and data between the probe and non-rotating equipment. Manufacturers often wish to use rotating systems that do not require slip rings to reduce the expense and maintenance high speed slip rings entail.

This can be accomplished by using the clear-through hole in spindle rotor 4 to transmit incident laser beam IB to a spinning reflector in probe tip 10 and transmit back reflected light RL through spindle rotor 4 to non-rotating optics, detector 24 and electronic circuit 21 on the other side of spindle 14 rather than using the clear-though hole in rotor 4 for electrical cables. This is shown for probe system 200 in FIG. 5. Doing this eliminates slip ring 23 but increases the optical path length between cylinder surface 9 and detector 24, increasing the sensitivity to alignment of the probe system. Using a larger diameter detector for detector 24 and a spindle with a rotor that is as short as possible consistent with probe stability to minimize optical path length can partially reduce this problem. The spindle can be smaller in this case than spindles supporting rotating probes containing a laser module, additional optical components and electronics because the spindle does not have to support the mass of a relatively large spinning probe.

Figure 5:
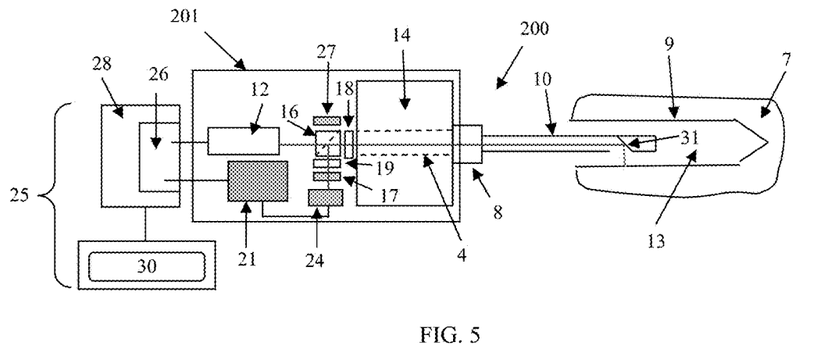
FIG. 5 is a schematic drawing of yet another inspection probe for the collection of back reflected light in accordance with the principles of the present invention.

Another alignment issue with the slip-ring-free approach is that the alignment between mirror 31 in spinning tip 10 and incident beam IB is not constant, since the mirror rotates relative to incident beam IB. Incident beam IB will be properly aligned relative to the rotating mirror in probe tip 10 only when incident beam IB hits the center of the rotating mirror. An advantage of placing the laser module, optics, detector and electronics in back of the spindle is that space for components needed to perform interferometric measurements can be more easily included in the probe design.

An additional potential advantage of having a scanning probe with non-rotating components is that a fiber laser can be used instead of a diode laser in laser module 12. When a fiber laser is used to generate a small laser spot on cylinder surface 9, the incident beam IB is not linearly polarized. For a circular laser beam half of incident beam IB is reflected by polarizing prism 16 and not transmitted to cylinder surface 9. To prevent this light from scattering inside the probe apparatus and affecting the operation of probe inspection system 200, the rejected laser light can be directed to beam dump 27, where it is absorbed. A high-absorption neutral density filter can be used as beam dump 27. Beam dump 27 can also be used to absorb unwanted reflected laser light if the polarization of a linearly polarized incident beam IB is not precisely aligned for maximum transmission through polarizing prism 16.

In FIG. 5, only probe tip 10 with reflector 31 is rotated by spindle 14 of probe 200. Tip 10 is mounted in spindle 14 using collet or other mounting system 8. Laser module 12, polarizing prism 16, quarter wave plate 18, highly-absorbing neutral density filter or beam dump 27, wavelength filter 19, optional neutral density filter 17, detector 24 and detector electronics 21 as well as spindle 14 are all mounted on non-rotating surface 201. Surface 201 can itself be mounted on a linear motion stage to move probe 200 relative to cylinder 13. Linear and rotary encoders that monitor the motion of the linear motion stage and the rotation of spindle 14 may also be employed.

Figure 6:
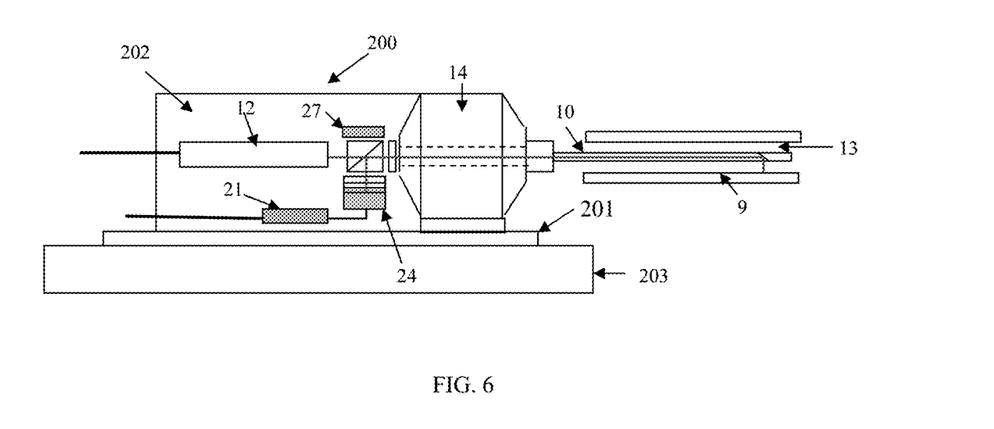
FIG. 6 is a schematic drawing of a side view of the probe shown in FIG. 5.

A schematic side view of probe 200 of FIG. 5 is shown in FIG. 6. In FIG. 6 the non-rotating components of the probe are contained in enclosure 202 that shields the components from room light, electrical noise and the outside environment. Surface mounting plate 201 can be mounted on linear motion stage 203 that moves probe 200 with spinning tip 10 into cylinder 13 to scan inside surface 9.

The probe embodiments that have been described up to this point can only be used to obtain two dimensional images of a cylinder surface, but may not be sufficient to determine displacement of the cylinder surface relative to the probe. Displacement information can be obtained from triangulation using scattered light, but cannot be used with back reflected light because triangulation requires having an angle between the incident beam IB and the return light RL to calculate displacement. However, using back reflected light it is possible to obtain displacement information from interferometry. This is shown in FIG. 7.

To obtain interference fringes, the light containing information about the surface, return light RL, and a reference beam must have the same direction of polarization at the detector. For a probe in which the incident beam IB and the return light RL are separated by a polarizing beam splitter 16 the transmitted component of IB and RL have mutually orthogonal polarizations. To generate a reference beam with the same direction of polarization as return light RL, the incident beam IB must be separable into components with orthogonal polarizations. This can happen if a fiber laser is used for laser module 12, since the light from a fiber laser is depolarized. This depolarized light can be split into its two polarization components by polarizing beam splitter 16. In this case the intensity of each component of polarization is equal. Two components of polarization can also be generated when laser module 12 generates linearly polarized light using a laser diode module if laser module 12 is rotated so that the light is split into two different directions of polarization by beam splitter 16. In this case the relative intensity of the different components can be varied by rotating laser module 12 relative to polarizing beam splitter 16.

In probes 15, 505 and 200 the direction of polarization of the component of incident beam IB transmitted through polarizing beam splitter 16 is orthogonal to the polarization of the component of the incident beam that is reflected by polarizing prism 16. Beams with orthogonal polarizations cannot interfere. But because quarter wave plate 18 rotates the polarization of return light RL relative to incident beam IB by 90°, the reflected component RB of incident beam IB and return light RL reflected by polarizing beam splitter 16 will have the same direction of polarization and can be made to interfere.

Figure 7:
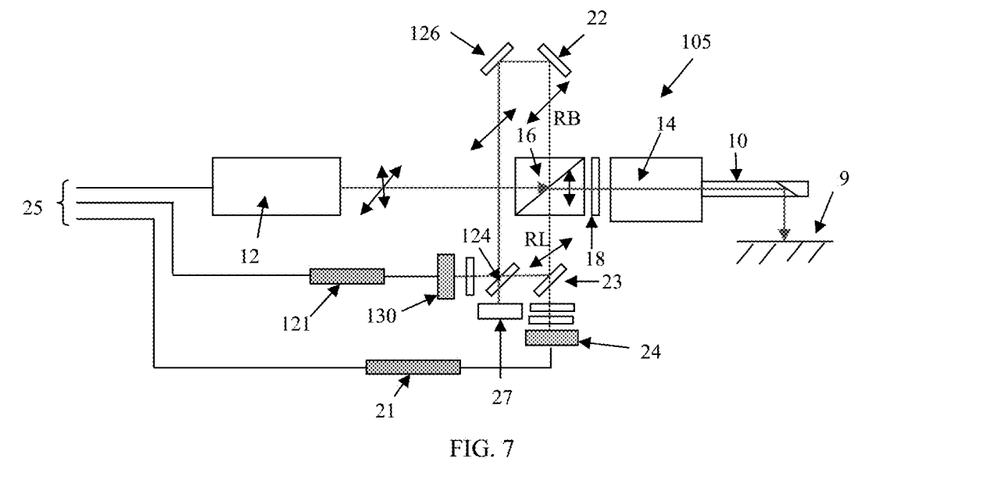
FIG. 7 is a schematic drawing of an inspection probe for detecting back reflected light that can also obtain profile information using interferometry.

Probe 105 in FIG. 7 is an extension of probe design 200 of FIG. 5. However, in probe 105 laser beam polarization is explicitly used to generate optical interference. In probe system 105, one component of polarization of incident beam IB is transmitted through polarizing beam splitter 16. The component of incident beam IB that is reflected by polarizing beam splitter 16 is rejected beam RB in FIG. 7. By utilizing rejected component RB of incident laser beam IB as a reference beam, an interference pattern can be generated with return light RL. This interference pattern can be employed to obtain additional profile information about surface 9.

In addition to the components of probe 200, the inspection system of probe 105 includes mirrors 126 and 22, partially transmitting mirrors 23 and 124 and detector 130 with its electronic circuit 121. Accordingly, rejected beam RB reflected from mirrors 22 and 126 is directed to partially transmitting mirror 124 from which a portion of rejected beam RB is directed to second detector 130, which is substantially similar to first detector 24. The rest of the beam energy that is not transmitted to second detector 130 is transmitted into beam dump 27, which can be a high-absorption neutral density filter.

Hence, part of return light RL and part of rejected beam RB will interfere. Thus, inspection system 105 can generate a fringe pattern detected using detector 130 as the laser probe scans surface 9 of cylinder 13 in addition to an image of surface 9 produced with data from detector 24.

Specifically, as incident beam IB scans cylinder surface 9 an image of the interference pattern is generated by the inspection system 105 from light collected by detector 130 and transmitted to data acquisition system 26. Since return light RL will be divided between two detectors, more weakly absorbing or no optional neutral density filters may be used in front of the detectors to prevent saturation of the signals in detectors 24 and 130.

The interference pattern obtained using detector 130 can be used to determine how well probe tip 10 is aligned relative to surface 9 of part 13. It can also be used to determine a surface profile that is different than the two dimensional image of surface 9. Since misalignment of probe 105 relative to cylinder 13 and the surface profile of cylinder surface 9 of cylinder 13 may have different characteristic patterns, misalignment can be subtracted from the profile generated from the data collected by detector 130 to produce only the surface profile.

Figure 8:
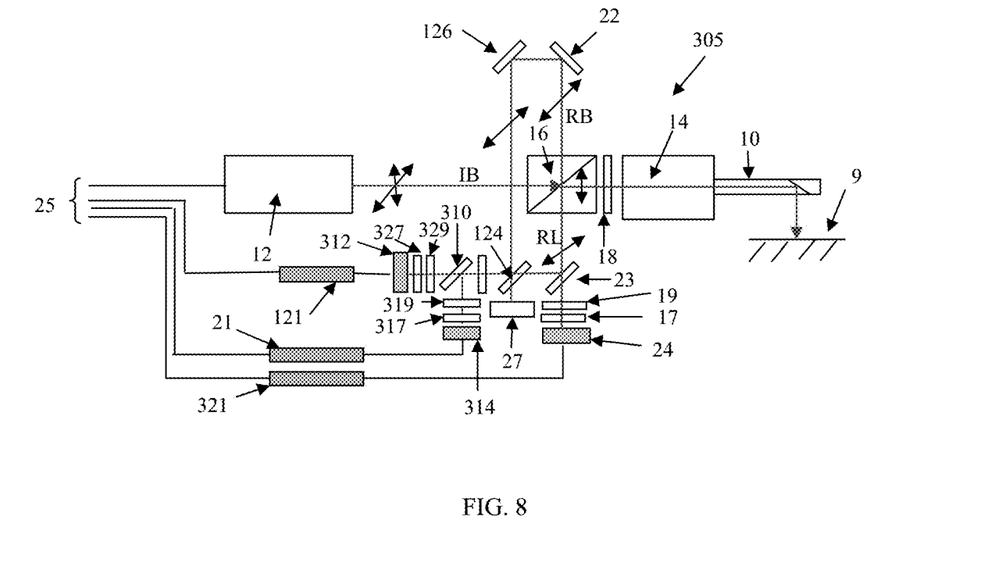
FIG. 8 is a schematic drawing of an inspection probe for detecting back reflected light at two different wavelengths of light to obtain more detailed profile information about a surface using interferometry.

In another arrangement, shown in system 305 of FIG. 8, two laser wavelengths are input simultaneously into a fiber laser 12 and a dichroic mirror 310 is used to separate the signals from the different wavelengths when measuring fringes. Other optical components that can separate monochromatic optical signals of different wavelengths from each other, such as prisms or diffraction gratings might be used instead of dichroic mirrors. Two detectors 312 and 314, instead of one detector 130, collect the different wavelengths of light that can be used to produce fringe patterns at the two different wavelengths. The additional information provided can be used to indicate whether surface 9 is moving closer to or farther from probe tip 10 as the probe system proceeds into cylinder 13.

Wavelength filter 19 permits only one of the wavelengths to reach detector 24. This is usually the shortest wavelength for higher resolution of the image of surface 9. A second wavelength filter 319 that permits the same wavelength of light to pass through as wavelength filter 19 can be used for one of the detectors collecting light from the dichroic mirror, which in FIG. 8 is labeled detector 314. An optional neutral density filter 317 can be used with wavelength filter 319 to control the amount of light reaching detector 314. A second wavelength filter 329 can be used to permit only the second laser wavelength to reach detector 312 after passing through optional neutral density filter 327.

In the examples of FIGS. 7 and 8, the optical components processing the signals obtained from cylinder surface 9 are non-rotating and located behind spindle 14. It is possible to mount the laser module, optical components and electronics inside a larger diameter cylindrical probe mounted on a larger, more robust spindle with a means of transmitting power in and data out, such as a slip ring. The larger diameter rotating probe then has a small diameter tip attached to the end of the probe, which fits into and scans the surface of a small diameter cylinder.

The description of the invention is merely exemplary in nature and variations that do not depart from the gist of the invention are intended to be within the scope of the invention. Such variations are not to be regarded as a departure from the spirit and scope of the invention.

What is claimed is:

1. A non-contact optical probe for inspecting an inside surface of a cylindrical workpiece comprising:
   a laser source that emits an incident light beam;
   a polarizing beam splitter that transmits one polarization of the incident beam and reflects an opposite polarization;
   a quarter wave plate that together with the polarizing beam splitter separates back reflected return light from the incident laser beam;
   an optical system that directs the incident laser beam onto the cylinder surface and directs reflected light from the surface back to the beam splitter, the optical system determining a solid angle of background light received by the detector to reduce sensitivity of the inspection system to alignment; and
   at least one detector that receives a portion of the back reflected light from the cylinder surface and generates data about the cylinder surface.

2. The probe of claim 1 in which the optical system determines the size of a spot on the surface of the cylinder being inspected.

3. The probe of claim 1 further comprising a beam dump that absorbs unwanted light.

4. The probe of claim 1 in which a tip is attached to the end of the probe to permit the probe to inspect the inside surface of smaller diameter cylinders.

5. A non-contact probe for inspecting an inside cylindrical surface of a workpiece comprising:
   a laser source that emits an incident light beam;
   a polarizing beam splitter that transmits one direction of polarization of the incident laser beam and reflects another direction of polarization;
   a quarter wave plate that converts the transmitted incident beam from linear polarization to circular polarization and a portion of the return beam from circular polarization to a linear polarization that is perpendicular to the linear polarization of the incident beam;

a first reflector that directs the incident light beam onto the cylindrical surface and receives reflected light from the cylindrical surface;

a second reflector that receives scattered light from the cylindrical surface;

a first detector that receives the return reflected light from the polarizing beam splitter; and a second detector that receives scattered light from the cylindrical surface that is deflected by the second reflector, the first detector and the second detector generating signals related to reflected and scattered scanning data from the cylindrical surface.

6. The non-contact probe of claim 5 wherein the second detector is the same type of detector as the first detector.

7. The non-contact probe of claim 5 further comprising a beam dump that absorbs unwanted light.

8. The probe of claim 1 further comprising a second optical system that combines a portion of the incident beam and a portion of the return light from the cylinder surface to generate an interference pattern from which displacement information of the surface of the cylinder is generated.

9. The probe of claim 8 further comprising one or more additional detectors that detect the incident reflected beam and the return light to obtain image and displacement data for the cylinder surface.

10. The probe of claim 8 wherein an incident beam containing more than one wavelength of light generates image and displacement data at more than one laser wavelength, the information from each wavelength being separable using one or more dichroic mirrors or other wavelength separating optical components.

11. The probe of claim 10 wherein light with one wavelength is directed to a first detector and light with a second wavelength is directed to a second detector to produce fringe patterns at the two wavelengths.

12. The probe of claim 10 wherein the signals from the two wavelengths are used to obtain displacement information of the surface of a cylinder.

13. A non-contact optical probe for inspecting an inside surface of a cylindrical workpiece comprising:

a laser source that emits an incident light beam;

a polarizing beam splitter that transmits one polarization of the incident beam and reflects an opposite polarization;

a quarter wave plate that together with the polarizing beam splitter separates back reflected return light from the incident laser beam;

an optical system that directs the incident laser beam onto the cylinder surface and directs reflected light from the surface back to the beam splitter, the optical system determining a solid angle of background light received by the detector to reduce sensitivity of the inspection system to alignment;

a second optical system that combines a portion of the incident beam and a portion of the return light from the cylinder surface to generate an interference pattern from which displacement information of the surface of the cylinder is generated; and at least one detector that receives a portion of the back reflected light from the cylinder surface and generates data about the cylinder surface.

14. The probe of claim 13 in which the optical system determines the size of a spot on the surface of the cylinder being inspected.

15. The probe of claim 13 further comprising a beam dump that absorbs unwanted light.

16. The probe of claim 13 in which a tip is attached to the end of the probe to permit the probe to inspect the inside surface of smaller diameter cylinders.

17. The probe of claim 13 further comprising one or more additional detectors that detect the incident reflected beam and the return light to obtain image and displacement data for the cylinder surface.

18. The probe of claim 13 wherein an incident beam containing more than one wavelength of light generates image and displacement data at more than one laser wavelength, the information from each wavelength being separable using one or more dichroic mirrors or other wavelength separating optical components.

19. The probe of claim 18 wherein light with one wavelength is directed to a first detector and light with a second wavelength is directed to a second detector to produce fringe patterns at the two wavelengths.

20. The probe of claim 18 wherein the signals from the two wavelengths are used to obtain displacement information of the surface of a cylinder.

* * * * *